(12) United States Patent
Mohiuddin et al.

(10) Patent No.: US 11,557,373 B2
(45) Date of Patent: Jan. 17, 2023

(54) SYSTEMS AND METHODS FOR SMART TESTING OF GENETIC MATERIALS

(71) Applicant: Specialty Diagnostic (SDI) Laboratories, Inc., Garden Grove, CA (US)

(72) Inventors: Ozman Mohiuddin, Redmond, WA (US); Sumi Thomas, Rancho Santa Margarita, CA (US)

(73) Assignee: Specialty Diagnostic (SDI) Laboratories, Inc., Garden Grove, CA (US)

( * ) Notice: Subject to any disclaimer, the term of this patent is extended or adjusted under 35 U.S.C. 154(b) by 0 days.

(21) Appl. No.: 17/566,850

(22) Filed: Dec. 31, 2021

(65) Prior Publication Data

US 2022/0122694 A1 Apr. 21, 2022

Related U.S. Application Data

(63) Continuation-in-part of application No. 16/990,366, filed on Aug. 11, 2020, now Pat. No. 11,255,762.

(51) Int. Cl.
*G01N 35/00* (2006.01)
*G16B 25/10* (2019.01)
(Continued)

(52) U.S. Cl.
CPC .......... *G16B 25/10* (2019.02); *G06K 9/6256* (2013.01); *G06N 20/00* (2019.01); *G16H 50/20* (2018.01)

(58) Field of Classification Search
CPC .. A61B 5/7264; A61B 5/7267; C12Q 1/6883; C12Q 1/6886; G01N 35/00584;
(Continued)

(56) References Cited

U.S. PATENT DOCUMENTS 5,366,896 A 11/1994 Margrey et al.
5,968,731 A 10/1999 Layne et al.
(Continued)

FOREIGN PATENT DOCUMENTS

WO 2017143182 8/2017
WO 2019102282 5/2019

OTHER PUBLICATIONS

Sara Jordan, Artificial Intelligence and the COVID-19 Pandemic, May 7, 2020.
(Continued)

*Primary Examiner* — Jill A Warden
*Assistant Examiner* — Dwayne K Handy
(74) *Attorney, Agent, or Firm* — Caldwell Intellectual Property Law

(57) ABSTRACT

A system for second lab testing of genetic materials is presented. The system includes a computing device configured to receive a specimen from a human subject and perform a smart test on the specimen. The smart test includes a first lab test configured to generate a first lab test identifying a first disease agent and a second lab test configured to generate a second lab test identifying a second disease agent, wherein identifying the second disease agent includes generating a second lab machine-learning model, training the second lab machine-learning model as a function of a second lab test training set, and outputting, as a function of the second lab machine-learning model, the second lab test result using specimen data as an input. The computing device is further configured to generate a smart test result as a function of the smart test.

18 Claims, 13 Drawing Sheets

(51) Int. Cl.
  *G06K 9/62* (2022.01)
  *G06N 20/00* (2019.01)
  *G16H 50/20* (2018.01)

(58) Field of Classification Search
  CPC ..... G01N 35/0099; G01N 2035/00831; G16H 50/20; G16B 25/10
  See application file for complete search history.

(56) References Cited

U.S. PATENT DOCUMENTS

| | | |
|---|---|---|
| 6,702,988 B1 | 3/2004 | Sagona et al. |
| 7,666,355 B2 | 2/2010 | Alavie et al. |
| 8,107,693 B2 | 1/2012 | Osborne et al. |
| 8,234,129 B2 | 7/2012 | Michon et al. |
| 8,357,538 B2 | 1/2013 | Self et al. |
| 8,862,448 B2 | 10/2014 | Holmes et al. |
| 9,958,466 B2 | 5/2018 | Dalbert et al. |
| 10,088,460 B2 | 10/2018 | Dewitte et al. |
| 10,283,217 B2 | 5/2019 | Lui et al. |
| 2009/0306543 A1 | 12/2009 | Flowey et al. |
| 2010/0099083 A1 | 4/2010 | Raeison et al. |
| 2011/0191768 A1 | 8/2011 | Smith |
| 2015/0363563 A1 | 12/2015 | Hallwachs |
| 2017/0175169 A1 | 6/2017 | Lee et al. |
| 2018/0286497 A1 | 10/2018 | Bauer et al. |
| 2020/0081023 A1 | 3/2020 | Holmes et al. |
| 2020/0124868 A1 | 4/2020 | Carrascal De Las Heras et al. |

OTHER PUBLICATIONS

PCT/US21/45309; International Search Report; dated Nov. 17, 2021; By: Authorized Officer Kari Rodriguez.

Patient Intake Process

Welcome to SDI Labs Patient Intake Process in partnership with UB LABORATORIES

First Name *
John

Last Name *
Doe

Date of Birth *
2001-01-01

Patient Intake Process

Hi! John Doe. Welcome to SDI labs COVID-19 screening process.

SYSTEMS AND METHODS FOR SMART TESTING OF GENETIC MATERIALS

CROSS-REFERENCE TO RELATED APPLICATIONS

This application is a continuation-in-part of Non-provisional application Ser. No. 16/990,366 filed on Aug. 11, 2020, and entitled "METHOD AND SYSTEM FOR CLASSIFYING SAMPLE DATA FOR ROBOTICALLY EXTRACTED SAMPLES," the entirety of which is incorporated herein by reference.

FIELD OF THE INVENTION

The present invention generally relates to the field of laboratory sample testing. In particular, the present invention is directed to systems and methods for smart testing of genetic materials.

BACKGROUND

The need for fast patient results is the key to controlling and maintaining infections rates low. Moreover, the need for accurate results is a major factor in containing infections. Currently, the average turnaround time for a SARS-COV-2 test is one day for priority patients and 3-5 days for other populations. There are several different types of tests in which each tests varies in turnaround time, accuracy, and method of testing. In a climate where faster turnaround times would help to isolate those who test positive quicker in order to prevent further spread, it would be an advantage to improve testing procedures to decrease turnaround times to obtain results as well as better data management to make better predictions as to potential "hot spots." Furthermore, it is important for labs to manage the data surrounding these samples in an efficient manner.

SUMMARY OF THE DISCLOSURE

In an aspect, a system for second lab testing of genetic materials is presented. The system includes a computing device configured to receive a specimen from a human subject and perform a smart test on the specimen. The smart test includes a first lab test configured to generate a first lab test identifying a first disease agent and a second lab test configured to generate a second lab test identifying a second disease agent, wherein identifying the second disease agent includes generating a second lab machine-learning model, training the second lab machine-learning model as a function of a second lab test training set, wherein the second lab test training set includes a human subject descriptive data with a second disease agent, and outputting, as a function of the second lab machine-learning model, the second lab test result using specimen data as an input. The computing device is further configured to generate a smart test result as a function of the smart test.

In another aspect, a method for second lab testing of extracted samples is presented. The method includes receiving, by a computing device, a specimen from a human subject, performing a smart test on the specimen, wherein the smart test includes a first lab test configured to generate a first lab test identifying a first disease agent and a second lab test configured to generate a second lab test identifying a second disease agent, wherein identifying the second disease agent includes generating a second lab machine-learning model, training the second lab machine-learning model as a function of a second lab test training set, wherein the second lab test training set includes a human subject descriptive data with a second disease agent, and outputting, as a function of the second lab machine-learning model, the second lab test result using the specimen as an input. The method further includes generating a smart test result as a function of the smart test.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
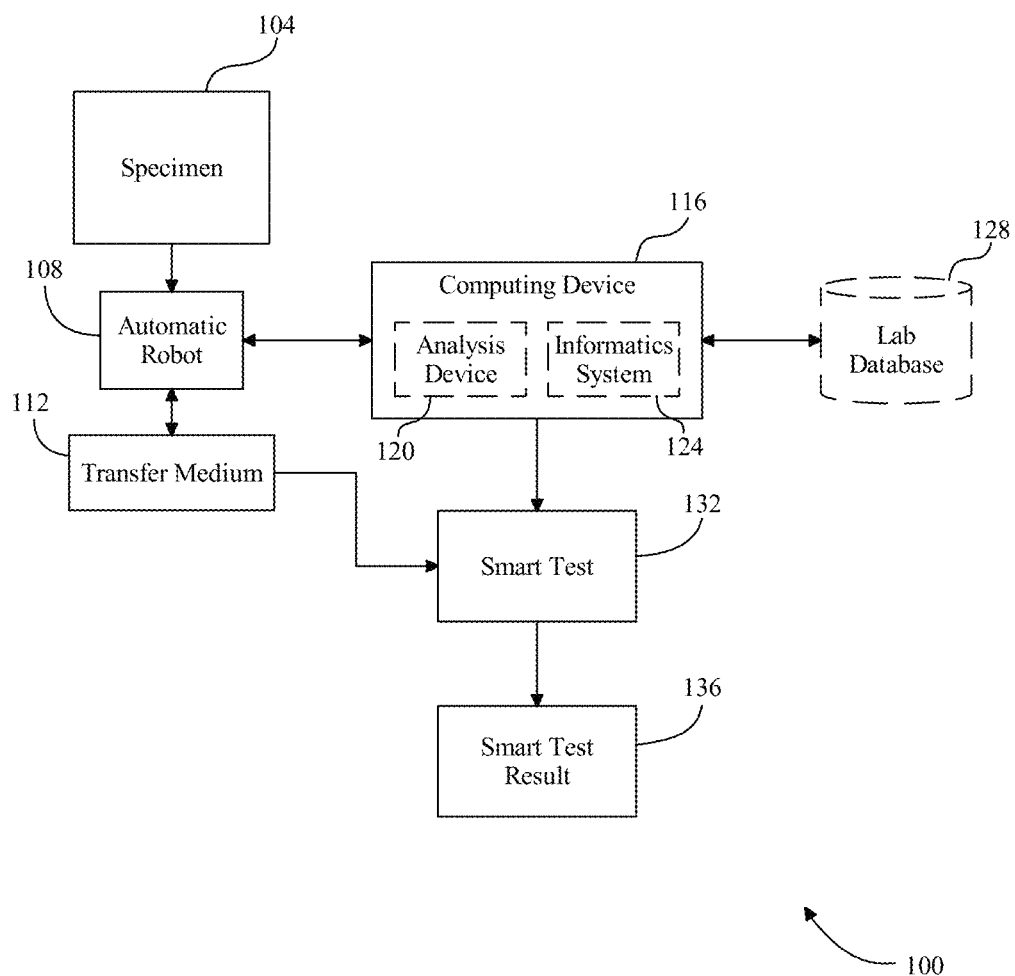
FIG. 1 is block diagram of an exemplary embodiment of a system for smart testing of genetic materials.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for smart testing of genetic materials. In an embodiment, the smart test may use genetic material extracted from a specimen such as a human subject. The genetic material may be stored in an isolated and contamination-free buffer configured to contain the extracted sample of the genetic material for prolonged testing and extending the life cycle of the extracted sample for several days. This is so, at least in part, because the buffer allows for multiple lab tests to be performed on the same human subject. The plurality of tests can identify a coronavirus (COVID-19/SARS-CoV-2) disease and any of its variations. A first lab test can include any rapid screen tests such as antigen test, a lateral flow immunoassay (LFIA), etc. The first lab test may be configured to provide quick results but may be less accurate compared to other tests. A second lab test can include any molecular diagnostic test such as a Reverse Transcription Polymerase Chain Reaction (RT-PCR) test. The second lab test may be configured to provide accurate and detailed results which may have a significantly longer turnaround time compared to the first lab test. A third lab test can include any respiratory pathogen (RP) test to check for any illness and/or disease in the respiratory tract of a human subject. In an embodiment, the third lab test may be configured to identify any respiratory related pathogens in addition to checking for sings of a coronavirus disease. One or more lab tests can be conducted using any machine-learning models, process, algorithms, or combination thereof.

Aspects of the present disclosure can also be used to classify sample data for samples extracted by using automatic robot 108. Testing includes specimens acquired from human subjects with each specimen containing genetic material for testing. Each sample includes an identifier which includes information about the human subject. Tests may be performed for one disease agent or a multiple disease agent where multiple disease agents may be identified by using a machine-learning model. If a positive result is obtained for a disease agent, an authorized person by human subject may be notified with an ability of the authorized person to have a conference event with, a medical professional such as without limitation a doctor.

Aspects of the present disclosure can also be used to combine and/or consolidate the test results of the smart test to provide a detailed report of the extracted sample of the human subject. In an embodiment, the resulting report can be generated using any machine-learning model, process, algorithm, or combination thereof. Aspects of the present disclosure can also be used to verify and/or validate each lab test of the smart test. In an embodiment, each lab test may be conducted independently from one another using the same extracted sample of the human subject. In another embodiment, each lab test may use different extracted samples of the same genetic material from the human subject. This is so, at least in part, to verify and/or validate the test results of each lab test and identify any discrepancies in the lab tests and/or extracted samples.

Referring now to FIG. 1, an exemplary embodiment of a system 100 for smart testing of genetic materials is illustrated. System includes a computing device 116. computing device 116 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device 116 may include a single computing device operating independently, or may include two or more computing device operating in concert, in parallel, sequentially or the like; two or more computing devices may be included together in a single computing device or in two or more computing devices. computing device 116 may interface or communicate with one or more additional devices as described below in further detail via a network interface device. Network interface device may be utilized for connecting computing device 116 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 116 may include but is not limited to, for example, a computing device or cluster of computing devices in a first location and a second computing device or cluster of computing devices in a second location. computing device 116 may include one or more computing devices dedicated to data storage, security, distribution of traffic for load balancing, and the like. computing device 116 may distribute one or more computing tasks as described below across a plurality of computing devices of computing device, which may operate in parallel, in series, redundantly, or in any other manner used for distribution of tasks or memory between computing devices. computing device 116 may be implemented using a "shared nothing" architecture in which data is cached at the worker, in an embodiment, this may enable scalability of system 100 and/or computing device.

With continued reference to FIG. 1, computing device 116 may be designed and/or configured to perform any method, method step, or sequence of method steps in any embodiment described in this disclosure, in any order and with any degree of repetition. For instance, computing device 116 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 116 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 116 may be configured to receive a specimen 104 from a human subject. As defined in this disclosure, a "specimen" is an element of biological material derived from a human. In a non-limiting embodiment, the human subject may have a potential infection may be caused by a plurality of disease agents. Specimen 104 may include any biological and/or genetic material. Specimen 104 may contain viral proteins and/or genetic material (including without limitation ribonucleic acid (RNA) and/or deoxyribonucleic acid (DNA)), and/or other proteins associated with disease agents, where disease agents may include pathogens such as bacteria, archaea, protists, fungi, infections proteins such as prions, parasitic multicellular organisms such as nematodes including without limitation ascarids and/or filarial worms, flatworms including without limitation flukes and tapeworms, insectoid parasites such as without limitation botflies and/or screw worms, or the like, potentially indicative of an infection. Examples of biological material collected as specimen 104 may include, but not limited to, blood, urine, fecal matter, tissues, organs, saliva, DNA/RNA, hair, nail clippings, or any other cell or fluids. Specimen 104 may come from either an adult or a child. Specimen 104 may be collected according to established protocols depending on the origin of the specimen. For example, collection of specimen 104 from the upper respiratory tract may use a nasopharyngeal swab method. Other examples of upper respiratory tract collection methods include, but are not limited to, a nasal mid-turbinate (NMT) swab and the nasopharyngeal wash, and/or the nasal wash/aspirate method. A lower respiratory tract sample may include the collection of sputum. Collection of a specimen 104 from the throat region may involve the use of the oropharyngeal swab method. Other methods of collection, including without limitation extraction of fluids, tissue samples, biopsies, or the like may be employed to collect specimen.

With continued reference to FIG. 1, specimen 104 may be collected from a third-party provider. Examples of third-party providers include nursing homes, a hospital, a drive-through site, a pharmacy, a healthcare professional's office, an urgent care facility, and the like. In a non-limiting embodiment, specimen 104 may be preserved by refrigeration with ice or by snap freezing the sample in a dry ice/ethanol slurry. In another non-limiting embodiment, specimen 104 may be shipped for analysis using services such as the United States Postal Service, or private couriers such as Federal Express, United Parcel Service, or the like. A "disease agent" as defined in this disclosure, is any organism that causes disease, such as bacteria, virus, fungus, or protozoa. Disease agents may be transmitted by, for example, skin contact, bodily fluids, airborne particles, contact with bodily fluids, and by contact with a surface originally touched by an infected person. Examples of disease agents include, but are not limited to Anthrax, Aspergillosis, Blastomycosis, Chicken pox, Adenovirus, Enterovirus, Rotavirus, Influenza, Coronaviridae such as, SARS-CoV-2 or any coronavirus, *Clostridium botulinum, Yersinia Pestis, Escherichia coli*, respiratory syncytial virus, mononucleosis, herpes, shingles, any respiratory pathogen, or any other disease agent described in this disclosure, and the like. In a non-limiting embodiment, specimen 104 may include genetic material collected from a human subject using a collection device and stored in a collection carrier. As used in this disclosure, "genetic material" is material used to store genetic information in the nuclei or mitochondria or an organism's cell. A "collection carrier," as used in this disclosure, is a device used to isolate and store biological material in an encapsulated space. Genetic material may include DNA and/or ribonucleic acid RNA. A potential infection may occur, for example, when a viral disease agent attaches to a specific host cell. Viral genetic information may then be inserted into a host cell where it starts to replicate, transcribe DNA into messenger RNA (mRNA) and translate mRNA into a viral protein. A new viral complex may then be released from the cell.

Still referring to FIG. 1, in an embodiment, specimen 104 may be received by a collection device. A "collection device," as used in this disclosure, is a device used to collect and store biological material for analysis. In a non-limiting embodiment, the collection device may include a swab and/or a transfer medium where the swab may be dipped in the transfer medium. In some embodiments, collection site may be used for testing may affect a type of swab used. Types of swabs that may be used include, but are not limited to, synthetic fiber swabs with plastic shafts such as COPAN FLOSwabs® 501CS01 for use in a nasopharyngeal site, a foam swab which may be used in nasal collection, and the like. Synthetic fibers used in swabs may include spun polyester fiber, spun rayon fiber, and the like. Swabs may be included as part of a disease agent testing kit. For example, a disease agent testing kit may include at least a swab, a sterile vessel that serves as a transport device, a transfer medium, a diagnostic requisition form, instructions, a unique identifier, and a bag for use to ship the sample to the testing laboratory. Sterile vessel may include without limitation a glass vial with a stopper, a plastic urine sample cup, a test tube, or the like.

With continued reference to FIG. 1, computing device 112 may receive extracted sample of a sequence of genetic material from specimen 104 using automatic robot 108. An "automatic robot," as used in this disclosure, is a mechanical and electrical device configured to extract genetic material for testing purposes. In a non-limiting embodiment, automatic robot 108 may include any instrumentation configured to monitor testing systems and processes for a smart test 132. In another non-limiting embodiment, automatic robot 108 may retrieve specimen 104 from a collection carrier and store it in a transfer medium 112. In another non-limiting embodiment, the use of the automatic robot 108 allows for high throughput testing. As defined in this disclosure, "high throughput" testing is the analysis of samples in a faster manner which allows for a testing and processing of more samples in less time. Extraction of sequence of genetic material includes a liquid extraction. High throughput may be achieved by working faster, analyzing multiple samples at once, or simultaneously handling multiple aspects of a sample at the same time. For liquid extraction, automatic robot 108 may be used. Use of automatic robot 108 may allow for dispensing precise amounts of specimen, reagents, or any other liquids to, for example, a well plate or a sample container. An example of automatic robot 108 used for preparation of liquid extraction may include the i-Pipette series by Apricot Designs™. Use of automatic robot 108 may provide for preparation and processing of between about 1,000 and about 10,000 samples per day, between about 1000 and about 7,000 samples per day, and/or between about 1,000 and about 3000 samples per day. Use of automatic robot 108 may provide for preparation and processing of between about 96 to about 1536 samples per hour; between about 96 to about 384 samples per hour; or between about 96 to about 192 samples per hour. In an embodiment, automatic robot 108 may process about 384 samples per hour. In another embodiment, automatic robot may process about 1536 samples per hour. A 3D printed plate with a capacity of 384 wells may be used to perform extraction. Commercial 384 well plates such as a Web Seal+384 Non Coated Plastic Microplate (Thermo Fisher Scientific) may be used. Well plates of other capacities such as, but not limited to, well plates having 96, 192, 1536, 3456, 6144 wells may be used.

Additionally, and still referring to FIG. 1, a Reverse Transcription-Polymerase Chain Reaction method may be used for the extraction (RT-PCR). (See, for example, The *CDC* 2019-*Novel Coronavirus* (2019-*nCoV*) *Real Time RT-PCR Diagnostic Panel*, released June 2020). One of ordinary skill, upon reviewing the entirety of this disclosure, will understand that this method may be utilized to convert an RNA sample to complementary DNA (cDNA) to provide a DNA template. One of ordinary skill, upon reviewing the entirety of this disclosure would understand that RT-PCR reagents are readily available from commercial vendors.

In a non-limiting example, a sample may be collected from a human subject by inserting a spun polyester swab with a plastic shaft into the nasopharyngeal cavity of a human subject. Post-sampling activities may include breaking plastic shaft in order to fit a sample into a sterile vessel which contains transfer medium. Swab may be dipped into transfer medium contained in transfer vessel. Transfer vessel may be sealed, and a unique identifier placed on sample, for instance in the form of a label, which may be alphanumeric and/or a machine-readable label such as without limitation a bar code and/or quick-read (QR) code. Sample and one or more diagnostic requisition forms may be placed in a bag; the bag may be shipped to a testing lab.

Alternatively or additionally, and with continued reference to FIG. 1, collection device may include blotting paper. As defined in the disclosure, "blotting paper" is paper that can be used for collection of biological materials. A non-limiting example of material that can be collected using blotting paper includes blood. An example of paper that can be used as blotting paper includes filter paper. Filter paper may be made from high purity cotton linters. As an example, to analyze for presence or absence of antibodies for the SARS-COV2 infection, a dried blood specimen 104 is collected by applying drops of a human subject's blood onto the blotting paper. Blood may be drawn by lancet from a finger, heel, toe, or the like. Once blood dries on paper, it may be shipped to a lab with a diagnostic requisition form and/or a unique identifier for analysis.

Alternatively or additionally, and further referring to FIG. 1, collection device may include a sterile dry container. Dry container may include any closure device to close dry container. These may include, but are not limited to, threaded closures, stoppers, metal caps, and the like. Collection device may contain sputum. As an example, a human subject may expectorate a sample of sputum into a dry container; once collected, the dry container containing the sputum may be shipped to a lab with a diagnostic requisition form and/or a unique identifier for analysis.

With continued reference to FIG. 1, the sequence of genetic material from specimen 104 may be stored in a transfer medium 112. A "transfer medium," as used in this disclosure, is a device or system used to maintain biological material. In a non-limiting embodiment, transfer medium 112 may store specimen 104. In another non-limiting embodiment, automatic robot 108 may extract a sequence of genetic material from specimen 104 and store it in transfer medium 112. Transfer medium 112 may include a plurality of storage units configured to organize and store a plurality of specimen 104. Transfer medium 112 may also be configured to maintain a certain temperature to prolong the life cycle of specimen 104. For example and without limitation, transfer medium 112 may house a plurality of collection carriers comprising a plurality of collection devices contaminated with biological material of a sequence of genetic material of specimen 104. In some embodiments, automatic robot 108 may individually store, retrieve, and/or move each collection carrier for analysis purposes. In a non-limiting embodiment, transfer medium 112 may include a buffer. The buffer may include a lysis buffer. As used in this disclosure, a "lysis" buffer is a buffer used for its ability to break up cells. Examples of a lysis buffer include, without limitation, an NP-40 lysis buffer, a sodium dodecyl sulfate (SDS) lysis buffer, an ammonium-chloride-potassium (ACK) lysing buffer, and the like. In a non-limiting embodiment, a buffer may include a phosphate buffered saline tablet, Hanks balanced salt solution with calcium and magnesium ions, distilled water, ProClin 300, and the like thereof. Transfer medium 112 may be configured to maintain the stability of specimen 104 for several days such as a period ranging from at least 5 to 7 days. Persons skilled in the art, upon reviewing the entirety of this disclosure, will be aware of storing biological material in a controlled system in the context of viral testing.

With continued reference to FIG. 1, computing device 116 may be configured to perform a smart test 132 using specimen 104. A "smart test," as used in this disclosure is a collection of individual lab tests used to measure specimen data. "Specimen data," as used in this disclosure are information describing the biological and genetic materials of specimen 104. Specimen data may include information indicating any pathogens, disease agents, and the like thereof. Specimen data may, in some embodiments, include data output by first laboratory test. In a non-limiting embodiment, computing device 116 may be configured to identify elements of a coronavirus disease from the measured specimen data. In a non-limiting embodiment, smart test 132 may include unique individual lab tests configured to identify a plurality of disease agents in specimen 104. In some embodiments, smart test 132 may be performed using automatic robot 108. For example and without limitation, automatic robot 108 may retrieve a collection carrier containing specimen 104 from transfer medium 112 for a first lab test. In another non-liming example a second lab test may use a different collection carrier containing specimen 104 from transfer medium 112. Persons skilled in the art, upon reviewing the entirety of this disclosure, will be aware of the various embodiments of lab tests in the context of viral testing.

Still referring to FIG. 1, smart test 132 may include a plurality of lab tests wherein each lab test may be configured to generate its own lab test result. In a non-limiting embodiment, a test result may be positive, negative, inconclusive, false positive or false negative. A positive test result, as defined by this disclosure is a test result where the disease agent or plurality of disease agents being tested are found in the specimen. For example, a positive test for SARS-CoV-2 may indicate that the genetic material extracted indicates a positive infection for SARS-CoV-2. In an embodiment, the test result is a positive result. A positive result may be obtained based on achieving a certain criterion established for a particular analysis. For example, a specimen is considered positive for 2019-nCoV if 2019-nCoV marker (N1, N2) cycle threshold growth curves cross the threshold line within 40.00 cycles (<40.00 Ct). Each individual disease agent test has an established criterion for a positive result.

Alternatively or additionally, with continued reference to FIG. 1, a test result may include a negative test result, defined by this disclosure as a test result where the disease agent or plurality of disease agents being tested are not found in the specimen. For example, a negative test for SARS-CoV-2 may indicate that the genetic material extracted indicates a negative infection for SARS-CoV-2. As a non-limiting example, a specimen may considered negative for SARS-CoV-2 if all 2019-nCoV marker (N1, N2) cycle threshold growth curves do not cross a threshold line within 40.00 cycles (<40.00 Ct) and an RNase P growth curve DOES cross the threshold line within 40.00 cycles (<40.00 Ct). Each individual disease agent test may have an established criterion for a positive result.

Alternatively or additionally, with continued reference to FIG. 1, an inconclusive test result, as defined by this disclosure is a test result where a disease agent or plurality of disease agents being tested are not clearly positive or negative. In an embodiment, test result may be inconclusive. For example, an inconclusive test result obtained for a specimen tested for SARS-CoV-2 antibodies may be due to not enough antibodies present in, for example, blood analyzed. It may not be clear if a level of antibodies would be high enough to indicate an infection.

Alternatively or additionally, with reference to FIG. 1, a test result may include a false positive. A false positive test result, as defined by this disclosure is a test result that shows an infection by a disease agent or plurality of disease agents when, for example, a control sample or a specimen should show a negative result. For example, while running a negative control sample, in which a negative result for a disease agent is expected, a positive result may be obtained instead.

Alternatively or additionally, still referring to FIG. 1, a false negative test result, as defined by this disclosure is a test result that does not shows an infection by a disease agent or plurality of disease agents when, for example, a control sample or specimen 104 actually should show a positive result. For example, while running a negative control sample, in which a negative result for a disease agent is expected, a positive result is obtained instead.

Still referring to FIG. 1, computing device 116 may establish communications that includes an authorized human subject contact as a function of a positive result. As defined in this disclosure, an "authorized human contact" is a person or plurality of person which are designated by the human subject to receive test results. An authorized contact may be an immediate family member such as, but not limited to, the human subject's mother, father, siblings, a spouse, grandparents, the human subject's children, and the human subject's in laws. An authorized contact may be a friend, any religious leader such as a priest, a Rabbi, or an Imam. An authorized contact may be a person or plurality of persons that may have had prior contact with the human subject that may have been potentially infected by a disease agent. An authorized contact may be a government official or agency responsible for the management of the public health system where the human subject potentially infected by a disease agent resides. An authorized contact may be a school principal, a school superintendent or college dean when, for example, the human subject is a student. An authorized human subject contact may be an expert such as, but not limited to a doctor, nurse, nurse practitioner, epidemiologists, and the like.

Alternatively or additionally, still referring to FIG. 1, computing device 116 may initiate a conferencing event with the authorized contact. A conferencing event may be a video conference, a telephone conversation, a text conversation, and the like. A "telehealth conferencing event," as defined in this disclosure, is a conferencing event arranged to discuss health-related issues. Conferencing event may take place between one or a plurality of authorized contacts. For example, after a positive result for a disease agent, a doctor and the human subject's spouse may engage in a telehealth to discuss a potential isolation plan for residents in the same household as the human subject with a potential infection for a disease agent.

Still referring to FIG. 1, computing device 112 may include an analysis device 120. An "analysis device," as used in this disclosure, is any device used for method development and validation, extractables and leachables, material characterization, failure analysis, and the like thereof, of biological material. In a non-limiting embodiment, analysis device 120 may determine a test result for a disease agent as a function of the sequence of generic material from specimen 104. Analysis device 120 may amplify and quantitate DNA. For example, analysis device includes a quantitative Polymerase Chain Reaction (qPCR) instrument or a real time PCR instrument with thermal control. Examples of real time PCR instruments include the LightCycler96 (Catalog No. 05815916001, Roche) or Thermo Fisher Scientific QuanStudio 5 Series qPCR system with 384 well plate capacity (Catalog No. A28140). As PCR progress is monitored by fluorescence, the real time PCR instrument may include a fluorimeter. As an example, RNA is converted to complementary DNA by reverse transcription. The PCR reaction amplifies and detects the sequence of interest which uses fluorescence reporters as a real time detection mechanism. Following the amplification of complementary DNA after a number of cycles, a sequence of interest, for example, for a disease agent of interest may be measured. For example, after 45 PCR cycles, the human subject specimen may generate a complementary DNA sequence that shows the presence of the SARS-CoV-2 viral DNA. This may indicate a positive result for the presence of the virus. In an embodiment, the test result is a positive result. In another embodiment, communications with an authorized human subject contact may be established as a function of the positive test result. Persons skilled in the art, upon reviewing the entirety of this disclosure, will be aware of the various embodiments of analyzing biological material for the existence of viral elements.

With continued reference to FIG. 1, analysis device 120 may perform a serological test on a blood sample to detect the presence of antibodies for a disease agent. For example, the analysis may look for antibodies against a disease agent like the SARS-CoV-2 virus for infections that have occurred in the past. A serological test may be performed using an enzyme-linked immunosorbent assay or ELISA-based test. An ELISA assay uses a solid-phase type of enzyme immunoassay (EIA) to detect the presence of a protein in a liquid sample using antibodies directed against the protein to be measured. Detection may be accomplished by measuring the activity of the reporter enzyme via incubation with the appropriate substrate to produce a measurable product. ELISA-based serological testing protocols for viruses, such as but not limited to, SARS-CoV-2 have been established by the Center for Disease Control (see, for example, "Serology Testing for COVID-19 at CDC").

Still referring to FIG. 1, specimen 104 may also include a unique identifier on the collection carrier human subject. As defined in this disclosure, a "unique identifier" is any identifier that refers to only one human subject. A unique identifier may include a specific sequence of characters, numbers, letters, and/or words that may identify a particular human subject. A unique identifier may include a globally recognized uniform identifier such as a uniform code commission (UCC) barcode. A unique identifier may include an optically captured and/or an otherwise captured identifier from a near field communication (NFC) tag or a radio frequency identifier (RFID) tag. As an example, a barcode containing human subject descriptive data may be included in the disease agent sampling kit which is used to acquire specimen 104. As defined in this specification, "human subject descriptive data" is defined as data that is unique to a particular human subject. Human subject descriptive data may include, but without limitation, a subject's name, contact information, ethnicity, number of people residing in the subject's household, and the like. Human subject descriptive data may further include, without limitation, the subject's symptoms, the subject's data of birth, any recent infections, any locations where the subject has travelled to, any known exposure to disease agents, medications, allergies, and the like.

Additionally or alternatively, and still referring to FIG. 1, human subject descriptive data may be collected from a human subject by the use of a web portal. As an example, and prior to sending a disease agent sampling kit, a medical facility may send the human subject a web link containing the universal resource locator (URL) address to the web portal used to collect the human subject descriptive data. Alternatively, a human subject may enter human subject descriptive data by using a computing device configured to receive the human subject descriptive data from the human subject. Computing device may use a machine-learning model and/or other automated process and/or program that receives responses from the human subject to questions and outputs iteratively further questions for the user to answer. For example, a selection of common medical conditions may be displayed to the human subject; the human subject may select conditions that are appropriate to that individual human subject.

Additionally or alternatively, and with further reference to FIG. 1, computing device 116 may be capable of compliance with security requirements of the Health Insurance Portability and Accountability Act (HIPAA). As an example, two step authentications may be required. Two-step authentication may ensure that the human subject is identified properly and to secure the information before the human subject sends human subject descriptive data or receives a response from the computing device. Other examples of security measures to protect the individual' data and privacy include, but are not limited to encryption of responses, requiring strong passwords, like 15-character passwords, or the like.

Additionally, or alternatively, and with continued reference to FIG. 1, human subject descriptive data may be stored in a laboratory information management system or LIMS. As used in this disclosure, a "laboratory information management system" is defined as a device that manages and stores data such as the human subject descriptive data, specimen information such as what disease agent to test, a human subject's test results, analytical methods used for clinical analysis, any instrumentation used for the clinical analysis, methods to validate results, and the like. A LIMS system may include a lab database 128, for instance as described in further detail below. The lab database 128 may contain human subject information stored in tables because of entries made by the human subject. For example, the human subject's ethnicity may be stored in the ethnicity table; the human subject's email address may be stored in the contact information table. As an example, once a human subject enters human subject descriptive data through a web portal application, the data may be stored in a secondary lab database 128 until sample is ready for testing. Once specimen 104 and/or sample is ready for testing, human subject descriptive data may be transferred to the lab database 128 in LIMS system. A unique identifier, such as a barcode, may match human subject's human subject descriptive data to specimen 104.

Still referring to FIG. 1, computing device 116 may retrieve human subject descriptive data as a function of the unique identifier. Human subject descriptive data collected from the human subject may be used to generate a human subject profile and used to generate the unique identifier such as, but not limited to a barcode. An input device may be used to acquire the unique identifier. A non-liming example of an input device may include an optical scanning device. An "optical scanning device," as defined in this disclosure, is a computing device that uses light, which may include actively generate and/or ambient light, to scan codes, text, or graphical images. An optical scanning device may be implemented as hardware or software. Examples of input optical scanning devices include, but are not limited to, a barcode reader, an image scanner, a light pen, a camera, or the like. Other input devices would depend on the type of unique identifier generated. For example, an RFID reader may be used to read an RFID tag when a unique identifier is an RFID tag. As the unique identifier may include and/or be associated with human subject descriptive data, which is stored in a lab database 128, once specimen 104 arrives in the laboratory, the identifier may be scanned using an input device to match the human subject descriptive data in the lab database 128 with the human subject descriptive data associated with the unique identifier. Specimen 104 may be tracked throughout the specimen's lifecycle in the laboratory.

Alternatively or additionally, and still referring to FIG. 1, computing device 116 may include an informatics system 124. As used in this specification, a "informatics system" is a tool for laboratory and data management which includes, but not limited to, workflow management, specimen tracking, process management, and the like. A non-limiting example of informatics system 124, include a laboratory information management system (LIMS).

Additionally or alternatively, and referring to FIG. 1, computing device 116 and/or informatics system 124 may further connect to and/or include a lab database 128. Lab database 128 may be implemented, without limitation, as a relational lab database 128, a key-value retrieval lab database 128 such as a NOSQL lab database 128, or any other format or structure for use as a lab database 128 that a person skilled in the art would recognize as suitable upon review of the entirety of this disclosure. Lab database 128 may alternatively or additionally be implemented using a distributed data storage protocol and/or data structure, such as a distributed hash table or the like. Lab database 128 may include a plurality of data entries and/or records as described above. Data entries in a lab database 128 may be flagged with or linked to one or more additional elements of information, which may be reflected in data entry cells and/or in linked tables such as tables related by one or more indices in a relational lab database 128. Persons skilled in the art, upon reviewing the entirety of this disclosure, will be aware of various ways in which data entries in a lab database 128 may store, retrieve, organize, and/or reflect data and/or records as used herein, as well as categories and/or populations of data consistently with this disclosure. In some embodiments, network data, or other information such as user information, courier information, and alimentary provider information, may be stored in and/or retrieved from lab database 128.

Alternatively or additionally, extraction may be sequenced by use of direct high-throughput sequencing using a lab database 128. In a non-limiting embodiment, lab database 128 may include a microbial-specific database. As a non-limiting example, a PMSeq® clinical database (BGI) may be used to compare extraction to a species information of suspected disease agentic microorganisms and provide information about a potential infection. Lab database 128 may divide detection process into a DNA detection process and an RNA detection process where the DNA detection process is used primarily for the detection of disease agents involving bacteria or fungi, proviruses, or the like. RNA detection process may be used for the detection of disease agents derived from RNA viruses. Sequencing may include analysis using other databases. Lab database 128 include, but are not limited to, a human genome lab database, such as, but not limited to the Genome Lab database 128; a disease agent genome lab database such as GeneDb; and a medical interpretation algorithm such as ChimeraSlayer, CATCh, or the like.

Still referring to FIG. 1, computing device may aggregate a plurality of human subject specimens into a single extraction. As defined in this disclosure, biological samples may be "pooled" when individual specimens are combined in, for example, one well of the well plate. An advantage of pooling specimen may be to use less reagents when running the analysis. The pooled samples may include specimens from the same human subject. The pooled samples may include samples from a plurality of human subjects. Another advantage is that it increases the efficiency and the throughput of the lab. A lab may pool between 2 and 10 specimens; between 2 and 8 specimens; or between 2 and 5 specimens. Specimens 104 may be pooled according to a disease agent of interest. As a non-limiting example, 5 specimens potentially infected with SARS-CoV-2 may be pooled together into a single well. Specimens 104 may be pooled by a descriptive human subject data. For example, several specimens may be pooled by zip code and tested for a variety of disease agents. A person of ordinary skill, having the benefit of the entirety of this disclosure, will be able to determine other methods of pooling specimens to test.

Still referring to FIG. 1, computing device 112 may be configured to generate a smart test result 136 as a function of smart test 132. A "smart test result," as used in this disclosure, is a consolidated and/or combined lab test result of smart test 132. Smart test result 136 may include a report containing a plurality of viral information of specimen 104 and the human subject. Smart test result 136 may include a positive and/or negative test result indicating the existence of a plurality of diseases agents. In a non-limiting embodiment, smart test 136 may include a severity level for the positive and/or negative test results. Persons skilled in the art, upon reviewing the entirety of this disclosure, will be aware of the various embodiments of a test result for a plurality of viral tests for purposes as described herein.

Figure 2:
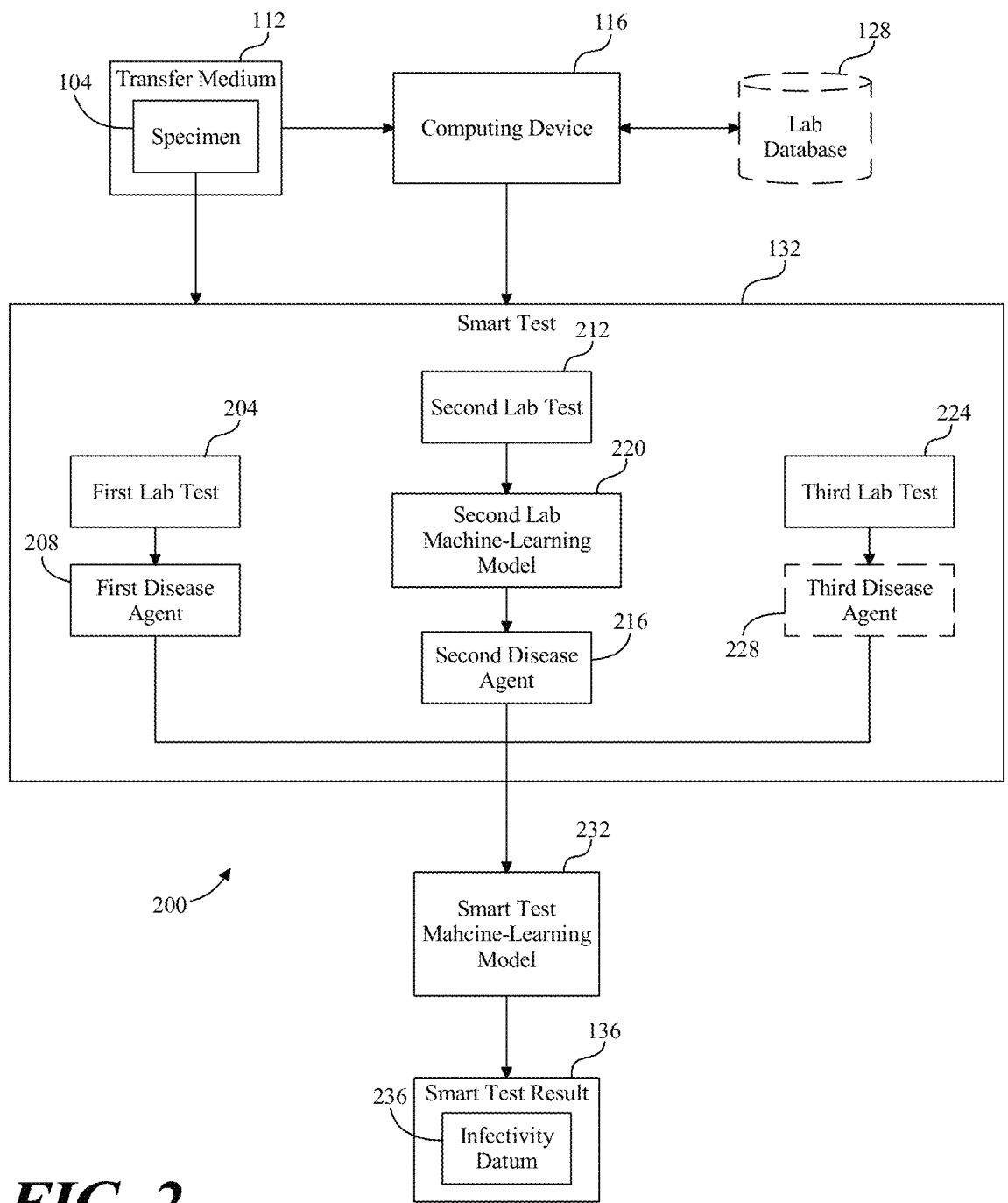
FIG. 2 is block diagram of another exemplary embodiment of a system for smart testing of genetic materials.

Now referring to FIG. 2, a block diagram of another exemplary embodiment of a system 200 for smart testing of genetic material is provided. System 200 may include smart test 132, wherein smart test 132 includes a first lab test 204, a second lab test 212, and a third lab test 224. In a non-limiting embodiment, smart test 132 may include additional lab tests. A "first lab test," as used in this disclosure, is an initial screen test used to quickly test specimen 104 for the identification of a first disease agent and generate a first lab test result. A "first disease agent," as used in this disclosure is any disease agent as described in the entirety of this disclosure identified from first lab test 204. A "first lab test result," as used in this disclosure, is any lab test result resulting from first lab test 204. The first lab test result may include an identification of first disease agent 208. In a non-limiting embodiment, first lab test 204 may include a rapid test for a viral infection to be able to quickly determine if a human subject is infected with a viral disease, such as a coronavirus disease. In another non-limiting embodiment, first lab test 204 may be designed and configured to be easy to use so that people with no special training can perform them and interpret the results. For example and without limitation, first lab test 204 may include any antigen test, lateral flow immunoassay (LFIA) test, lateral flow test (LFT), lateral flow device (LFD), lateral flow assay (LFA), lateral flow immunoassay (LFIA), Lateral flow immunochromatographic assays, dipstick, express test, pen-side test, quick test, test strip. And the like thereof. In another non-limiting embodiment, first lab test 204 may include at-home tests, home collection tests, prescription tests, non-prescription tests, Direct to Consumer (DTC) Test, and the like thereof. First lab test 204 may be configured to be the most flexible and/or available lab test for human subjects. For example and without limitation, any human may perform first lab test 204 at home, a testing site, a laboratory, and the like thereof. In some embodiments, first lab test 204 may be performed without using computing device 116. Persons skilled in the art, upon reviewing the entirety of this disclosure, will be aware of the various embodiments of rapid antigen testing in the context of viral testing.

With continued reference to FIG. 1, computing device 116 may be configured to perform a second lab test 212. A "second lab test," as used in this disclosure, is an antigen test used to amplify genetic material to identify a second disease agent and generate a second lab test result. A "second disease agent," as used in this disclosure, is any disease agent as described in the entirety of this disclosure identified from second lab test 212. A "second lab test result," as used in this disclosure, is any lab test result used to identify a second disease agent. In a non-limiting embodiment, second lab test 212 may be designed and configured to provide accurate test results and be conducted by a skilled worker, requiring extensive sampling. For example and without limitation, second lab test 212 may include a real-time reverse transcription polymerase chain reaction (rRT-PCR) test. In a non-limiting embodiment, second lab test 212 may be performed using a technique called a polymerase chain reaction. For example and without limitation, a health care worker takes the sample and treats it with an enzyme that converts RNA into double-stranded DNA. Then, the DNA is mixed with a solution containing an enzyme called a polymerase and heated, causing the DNA to separate into two single-stranded DNA pieces. The temperature is lowered, and polymerase, with the help of a small piece of guide DNA called a primer, binds to the single-stranded DNA and copies it. The primers ensure that only coronavirus DNA is amplified. The result may include two copies of coronavirus DNA from the original one piece of RNA. The amplifying property of PCR allows the test to successfully detect even the smallest amount of coronavirus genetic material in a sample. This makes it a highly sensitive and accurate test. With accuracy that approaches 100%, it is the gold standard for diagnosing SARS-CoV-2. Persons skilled in the art, upon reviewing the entirety of this disclosure, will be aware of the various embodiments of a better performing antigen test in the context of improving test results for viral testing.

Still referring to FIG. 2, computing device 116 may identify second disease agent 216 as a function of descriptive data and second lab machine-learning model 220. In a non-limiting embodiment, computing device 116 may output second disease agent 216 that is identical to first disease agent 208 and/or second disease agent 216 that is distinct from the first disease agent 208. For example and without limitation, a positive result for first disease agent 208 may result when an identity of second disease agent 216 is identical to the identity of first disease agent 208 and there is a positive result for the presence of second disease agent 216. In a non-limiting embodiment, second lab test 212 may be performed after performing first lab test 204 as a function of a time delay. The time delay may include a delay of any amount of time between first lab test and second lab test, including without limitation delays of several hours or several days. For example and without limitation, second lab test 212 may wait a period of time after first lab test 204 is performed in order to verify the results of second lab test 212 and/or validate the results despite extended existence of a coronavirus disease of specimen 104. Persons skilled in the art, upon reviewing the entirety of this disclosure, will be aware of the various factors such as time in the context of viral testing.

Alternatively or additionally, and with continued reference to FIG. 2, computing device 116 may determine a presence of first disease agent 208 and second disease agent 216 in specimen 104 based on a comparison of the identity of first disease agent 208 and second disease agent 216. For example and without limitation, second lab machine-learning model 220 may receive human subject descriptive data as an input and outputs a second lab test that identifies second disease agent 216 wherein second disease agent 216 is identical to first disease agent 208. In a non-limiting embodiment, computing device 116 may receive genetic material from specimen 104 as an input and generate second lab machine-learning model 220. Computing device 116 may train second lab machine-learning model 220 as a function of a human subject descriptive training data. A "human subject descriptive training data," as used in this disclosure, is a training set that correlates human subject descriptive data with a second disease agent. In a non-limiting embodiment, computing device 116 may retrieve the human subject descriptive training data from lab database 128. Persons skilled in the art, upon reviewing the entirety of this disclosure, will be aware of the various embodiments of a training data in the context of identifying a disease agent for purposes as described herein.

With continued reference to FIG. 2, computing device 116 may be configured to perform a third lab test 224. A "third lab test," as used in this disclosure is any pathogen test distinct from first lab test 204 and/or second lab test 212 that identifies a third disease agent 228. A "third disease agent," as used in this disclosure, is any disease agent as described in the entirety of this disclosure identified by third lab test 224 In a non-limiting embodiment, third lab test 224 may include any respiratory pathogen test. For example and without limitation, third lab test 224 may receive only a single extracted sample of genetic material of specimen 104 and run tests for a wide variety of viruses and bacteria. Turnaround time for results from third lab test 224 may take a few hours or several days. Third lab test 224 may be designed and configured to identify a plurality of respiratory pathogen viral and bacterial infections such as, but not limited to, flu, common cold, respiratory syncytial virus (RCV), adenovirus infection, COVID-19, pneumonia, and the like thereof. Persons skilled in the art, upon reviewing the entirety of this disclosure, will be aware of the various embodiments of a third test in the context of generating improved test results.

Still referring to FIG. 2, computing device 116 may perform a textual conversation with a user, the textual conversation including transmitting to a computing device, a plurality of potential user symptoms and receiving a user selection of a potential user symptom from the plurality of user symptoms. A "textual conversation," as defined in this disclosure, is a conversation involving either text or messaging that is interactive. Inputs and/or outputs may be exchanged iteratively using, for example, messaging services and/or protocols, including without limitation any instant messaging protocols. Based on inputs received from user, system may determine what the potential symptoms are. Persons skilled in the art, upon reviewing the entirety of this disclosure, will be aware of a multiplicity of communication protocols that may be employed to exchange text messages as described herein. Text messages may be provided in textual form and/or as audio files using, without limitation, speech-to-text and/or text-to-speech algorithms.

Alternatively or additionally, with continued reference to FIG. 2, a textual conversation may include one or more image files. Image file formats include, but not limited to, Joint Photographic Experts Group (JPEG), Portable Network Graphics (PNG), Graphics Interchange Format (GIF), Tagged Image File (TIF), Portable Document Format (PDF), Encapsulated Postscript (EPS), Raw Image Files (RAW), or the like. A user may capture an image using a device using a computing device. Devices may include, without limitation a mobile camera, a scanner, a digital camera, a tablet computer, or the like. For example, a human subject may take a picture of a certain area of their body and include the picture in the textual conversation.

Alternatively or additionally, with reference to FIG. 2, a user may initiate a textual conversation by using a text messaging protocol; Text messaging may include instant messaging protocol, such as, but not limited to Bitmessage, Bonjour, Matrix, short message service (SMS), or the like. Text messages can be classified in different categories depending on the subject of the message by processing the messages using, for example, natural language processing. Text messages and/or textual communication may include, without limitation, messages displayed and/or received using audio input and/or output devices, including using text-to-speech and/or speech-to-text technology.

Still referring to FIG. 2, computing device 116 may generate a recommendation for the human subject, wherein the second disease agent has a different identity from the first disease agent in the analyzed extracted sequence of generic material. For example, classifier may output a second disease agent that is different to the first disease agent. An identity of second disease agent may not match an identity of first disease agent. As defined in this disclosure, a "recommendation" may include one or a plurality of treatment care instructions based on an identity of the second disease agent. Recommendations may be identical to recommendations given for first disease agents. Recommendations may be based on input of symptoms from human subject. Recommendations may not correspond to a medical recommendation. For example, a non-medical recommendation may be to "isolate" or to "drink more fluids. A medical recommendation, for example, may instruct a human subject to "take a pain reliever" or to "schedule an appointment with a health professional." Negative results for a first disease agent may be compared against a plurality of symptoms stored in a symptoms table in a lab database 128. Another liquid extraction to test for a different disease agent may result.

Still referring to FIG. 2, computing device 116 may determine a human subject contact profile. As defined in this disclosure, a "human subject contact profile" is a profile that includes human subject data describing information that may be used to generate contact tracing information. Data may include, but not limited to, places where human subject has travelled to, their home address, number of people that live in the human subject home, the name of the people that live in the human subject's home, the work address of the human subject, name of immediate supervisor, and the like. Determining the human subject contact profile may include prompting a human subject for intake data and receiving human subject intake data as a function of the prompting for intake data. Intake data may have the same form and content as human subject descriptive data. Determining the human subject contact profile may include generating a contact machine-learning process as a function of contact training data. The contact training data may correlate intake data elements with a human subject contact profile elements. The human subject contact profile is determined as a function of the human subject intake data and the contact machine-learning process. The machine-learning process is as described above.

With continued reference to FIG. 2, computing device 116 may be configured to generate smart test result 136 as a function of smart test 132. Smart test result 136 may be consistent with any smart test result as described herein. In a non-limiting embodiment, smart test 136 may be designed and configured to provide a consolidated and/or combined test result of smart test 132. For example and without limitation, a few antigen tests are already available over the counter, in which smart test 136 may provide a better understanding of how each lab test performs at various stages of infection. In a non-limiting embodiment, smart test 136 may be generated as a function of a smart test machine-learning model 232. For example and without limitation, computing device 116 may generate smart test machine-learning model 232, wherein smart test machine-learning model 232 may receive a plurality of lab test results from smart test 132 as an input. Computing device 116 may train smart test machine-learning model 232 as a function of a smart test training set. A "smart test training set," as used in this disclosure is, a training set that correlates a disease agent data to an infectivity datum. A "disease agent data," as used in this disclosure is any data describing results of each lab test of smart test 132 which may identify any disease agent. In some embodiments, the smart test training set may be retrieved from lab database 128. In a non-limiting embodiment, disease agent data may include information regarding patient demographic data, community infectivity rates of various viral infections, known exposure to a person with a viral infection, symptomatic complaint, and the like. Smart test machine-learning model 232 may output smart test result 136, wherein smart test result comprises an infectivity datum 236. An "infectivity datum," as used in this disclosure, is a collection of information describing the results of the plurality of lab test results of smart test 132. In a non-limiting embodiment, infectivity datum 236 may include a plurality of severity levels indicating the level of severity of any pathogen and/or diseases, such as a coronavirus disease. In another non-limiting embodiment, infectivity datum 236 may include a measured coronavirus data. A "measured coronavirus data," as used in this disclosure, is any information describing the pathogens, severity, and/or any related information of a disease agent indicating the existence of a coronavirus disease. In a non-limiting embodiment, smart test result 136 may include a report of all findings of the smart test. For example and without limitation, smart test result 136 may include a verification and/or validation of each lab test result of the plurality of lab test results. As used in this disclosure, "verification" is a process of ensuring that which is being "verified" complies with certain constraints, for example without limitation system requirements, regulations, and the like. In some cases, verification may include comparing a product, such as without limitation each lab test result of the plurality of lab test results, against one or more acceptance criteria. For example, in some cases, each lab test result, may be required to follow some pathogen related and/or biological behavior criteria indicative of a disease agent. Ensuring that each lab test is in compliance with acceptance criteria may, in some cases, constitute verification. In some cases, verification may include ensuring that data is complete, for example that all required data types, are present, readable, uncorrupted, and/or otherwise useful for computing device 116. In some cases, some or all verification processes may be performed by computing device 116. In some cases, at least a machine-learning process, for example a machine-learning model, may be used to verify. Computing device 116 may use any machine-learning process described in this disclosure for this or any other function. In some embodiments, at least one of validation and/or verification includes without limitation one or more of supervisory validation, machine-learning processes, graph-based validation, geometry-based validation, and rules-based validation. As used in this disclosure, "validation" is a process of ensuring that which is being "validated" complies with stakeholder expectations and/or desires. Stakeholders may include users, administrators, property owners, customers, and the like. Very often a specification prescribes certain testable conditions (e.g., metrics) that codify relevant stakeholder expectations and/or desires. In some cases, validation includes comparing a product, for example without limitation, each lab test result against a specification. In some cases, computing device 116 may be additionally configured to validate a product by validating constituent sub-products. In some embodiments, computing device 116 may be configured to validate any product or data, for example without limitation, each lab test result. In some cases, at least a machine-learning process, for example a machine-learning model, may be used to validate by computing device 116. Computing device 116 may use any machine-learning process described in this disclosure for this or any other function. Persons skilled in the art, upon reviewing the entirety of this disclosure, will be aware of the various embodiments of a consolidated and/or combined report and/or test results of a plurality of lab test results in the context of accurate and improved viral testing.

Figure 3:
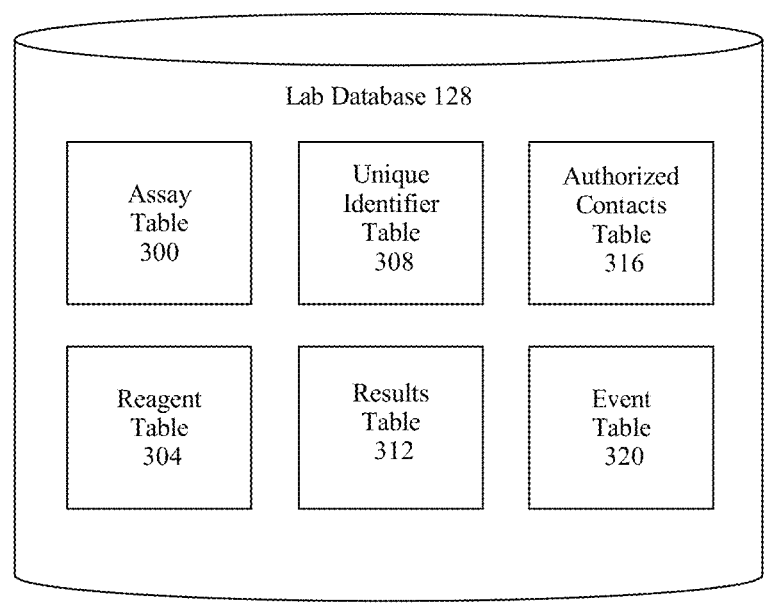
FIG. 3 is block diagram of an exemplary embodiment of a lab database.

Referring now to FIG. 3, a block diagram of an exemplary embodiment of a lab database 128 is illustrated. Lab database 128 may, as a non-limiting example, organize data stored in the database according to one or more database tables. One or more database tables may be linked to one another by, for instance, common column values. For instance, a common column between two tables of lab database 128 may include an identifier of a human subject, such as a unique identifier or the like, for instance as defined below; as a result, a query may be able to retrieve all rows from any table pertaining to a given human subject's specimen or previous specimens. Other columns may include any other category usable for organization or subdivision of data, including types of data, common pathways between, for example, a human subject's contacts and any previous infection of any of those contacts, other previous infections by the human subject, or the like; persons skilled in the art, upon reviewing the entirety of this disclosure, will be aware of various ways in which expert data from one or more tables may be linked and/or related to expert data in one or more other tables.

Still referring to FIG. 3, one or more database tables in lab database 128 may include, as a non-limiting example, an assay table 300, which may be used to store biological assays which may be used in testing a specimen. This may include, but not limited to, a particular virus assay such as Influenza or SARS-CoV-2, a bacterial assay such as Botulism. or the like. As another non-limiting example, one or more tables in lab database 128 may include a reagent table 304 which may be used to store inventory information as to what reagents are used for a particular assay. As another non-limiting example, one or more tables in lab database 128 may include a unique identifier table 408. A unique identifier table 308 may include, but not limited to unique identifier information that may associate a unique identifier to the specimen of a human subject. As another non-limiting example, one or more tables in lab database 128 may include a results table 312. A results table 312 may include results regarding a specimen, or the like. As another non-limiting example, one or more tables in lab database 128 may include an authorized contact table 316. An authorized contact table 416 may include, but not limited to, the list of authorized contact information which may include names and contact information of authorized contacts to receive specimen results, preferred method of contact, or the like. As another non-limiting example, one or more tables in lab database 128 may include an event table 320. An event table 320 may contain events related to the lifecycle of a specimen from the moment the specimen is received in the lab to the time a result is obtained. For example, events may include "on hold," "testing in process," "testing completed," or the like.

Figure 4:
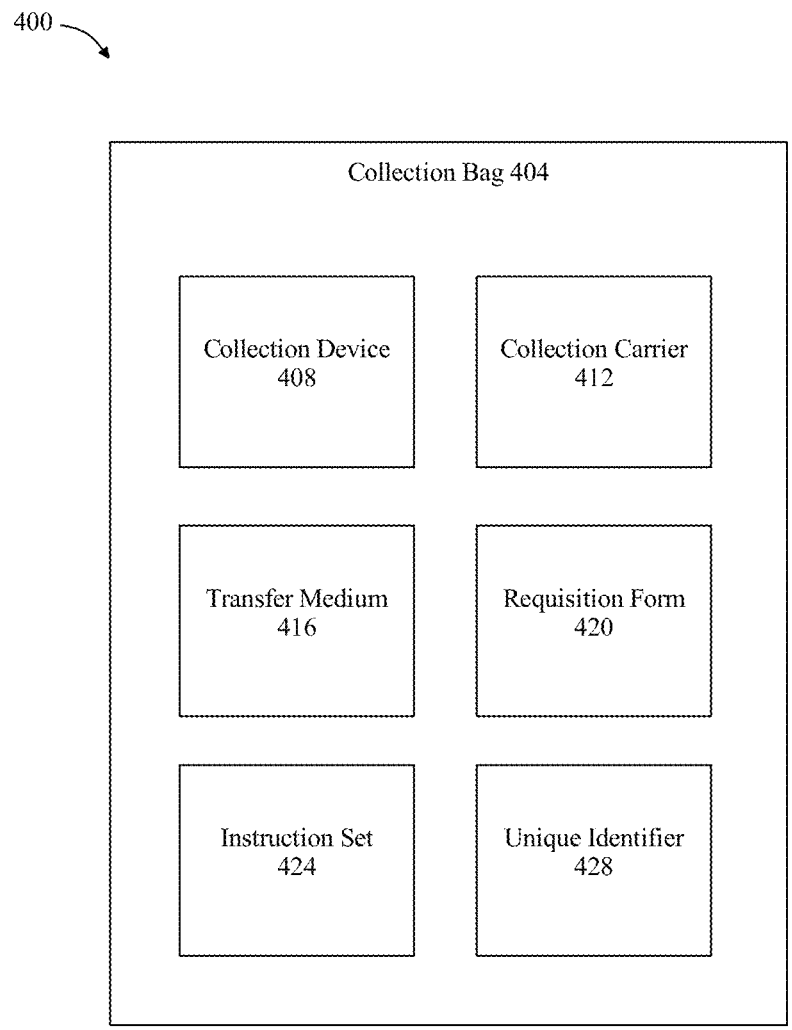
FIG. 4 is a block diagram of an exemplary embodiment of a collection kit.

Now referring to FIG. 4, the content of collection kit 400 that may be used to collect a specimen is described. The specimen may be consistent with specimen 104. The contents of a collection kit are included in a biohazard collection bag 404. The collection bag 404 may be of any color. The collection bag 404 may be made out of polypropylene, high density polyethylene, polyethylene, or the like. The collection bag 404 may be self-sealing; may seal using an airtight pressure closure, or the like. The collection bag 404 may be of any size, such as a 6"×9" bag. The collection bag 4504 may include a collection device 408. A collection device 408 may include a swab, blotting paper, or the like. Collection bag 404 may also include a collection carrier 412. In an embodiment, specimen 104 includes genetic material collected from the human subject using a collection device 408 and stored in collection carrier 412. In an embodiment, collection device 408 may include a swab and a transfer medium where the swab is dipped in the transfer medium. Collection carrier 412 may include a sterile vessel can be a glass vial with a stopper, a plastic urine sample cup, a test tube, or the like. A typical volume of a collection carrier 412 may be, but not limited to, 90 mL.

Alternatively or additionally, and still referring to FIG. 4, collection bag 404 may include a vial containing a transfer medium 416. Transfer medium 416 may be consistent with transfer medium 112 as described above. In another embodiment, collection device 408 may include a swab and a transfer medium where the swab is dipped in the transfer medium. In another embodiment, collection device 408 may be blotting paper. Collection device 408 may be consistent with any collection device as described herein.

Alternatively, or additionally, and still referring to FIG. 4, collection kit 400 may include a requisition form 420. Requisition form 416 may include information from the human subject about specimen 104. For example, requisition form 416 may include, but not limited to, information regarding the type of analysis or plurality of analyses requested, a description of specimen 104, the name of the person requesting the analysis, and the like. Collection bag 404 may include instruction set 424 on how to conduct the acquisition of specimen 104. As a non-limiting example, instructions on how to acquire a sample from the nasopharynx region may be included. Instruction set 424 may be written in a foreign language. For example instruction set 420 included in collection kit 400 may be written is Spanish, Chinese-Mandarin, Chinese Cantonese, Japanese, Vietnamese, French, Italian, and the like.

Alternatively or additionally, and still referring to FIG. 4, collection kit 400 may include a unique identifier 428. Unique identifier 428 may be consistent with any unique identifier as described herein. In an embodiment, specimen 104 include unique identifier 428 on collection carrier 412. Unique identifier 428 may contain human subject descriptive data. For example, collection kit 400 may contain a barcode. The barcode would associate specimen 104 with a human subject. The barcode would be used to track the sample through the lifecycle of the sample.

Figure 5:
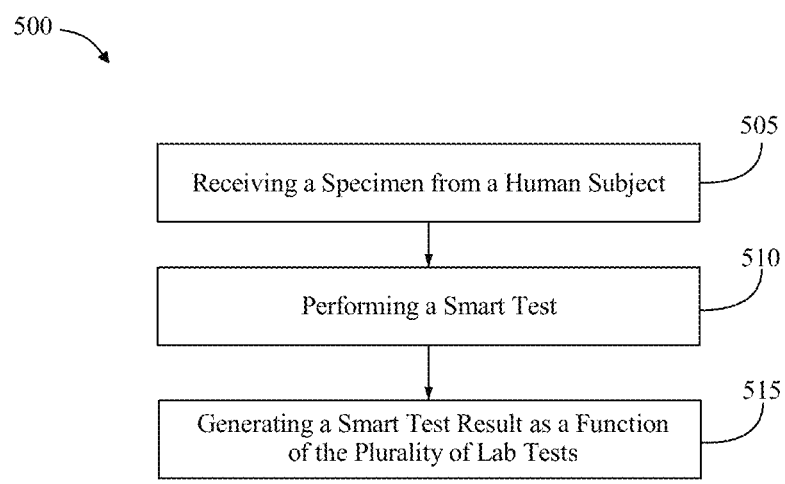
FIG. 5 is a flow diagram of an exemplary embodiment of a method for smart testing of genetic materials.

Referring now to FIG. 5, a flow diagram of an exemplary method 500 of smart testing of genetic materials is provided. Method 500, at step 505, includes receiving, by a computing device, a specimen from a human subject. The computing device may include any computing device as described herein. The specimen may be consistent with any specimen as described in the entirety of this disclosure. In a non-limiting embodiment, method 500 may include extracting, by an automatic robot, a sequence of genetic material from the specimen. The automatic robot may include any automatic robot as described herein. The sequence of genetic material may include any sequence of genetic material as described herein. In a non-limiting embodiment, receiving the specimen may include receiving genetic material collected from the human subject using a collection device and stored in a collection carrier and a unique identifier on the collection carrier. The collection device may include any collection device as described herein. The collection carrier may include any collection carrier as described herein. In a non-limiting embodiment, method 500 may include storing the specimen in a transfer medium, wherein the transfer medium is configured to preserve the specimen for the plurality of lab tests. The transfer medium may include any transfer medium as described herein. Persons skilled in the art, upon reviewing the entirety of this disclosure, will be aware of the various embodiments extracting biological material from a human subject.

Still referring to FIG. 5, method 500, at step 510, may include performing a smart test on the specimen. The smart test may be consistent with any smart test as described herein. In a non-limiting embodiment, the smart test may include a first lab test, wherein the first lab test is configured to identify a first disease agent and a second lab test, wherein the second lab test is configured to identify a second disease agent. The first lab test may be consistent with any first lab test as described in the entirety of this disclosure. The first disease agent may include any first disease agent as described herein. The second lab test may be consistent with any second lab test as described in the entirety of this disclosure. The second disease agent may include any second disease agent as described herein. In a non-limiting embodiment, identifying the second disease agent may include generating a second lab machine-learning model, training the second lab machine-learning model as a function of a second lab test training set, wherein the second lab test training set includes a human subject descriptive data with a second disease agent, and outputting, as a function of the second lab machine-learning model, the second lab test result using specimen data as an input. The second lab machine-learning model may include any second lab machine-learning model as described herein. Specimen data may include any specimen data as described herein. In a non-limiting embodiment, specimen data may include a sequence of genetic material from a specimen. In another non-limiting embodiment, specimen data may include human descriptive data and/or any descriptive data as described herein. Method 500 may include retrieving the second lab test training data from a lab database, wherein the second lab training set may include previous iterations of methods as described herein. The lab database may include any lab database as described herein. Method 500 may further include retrieving the second lab test training data from use inputs. In a non-limiting embodiment, performing the smart test may include performing a third lab test configured to identify a third disease agent. The third lab test may include any third lab test as described herein. The third disease agent may include any third disease agent as described herein. In some embodiments, performing each lab test such as the first lab test, the second lab test, and/or the third lab test, may include performing each of them independently. In another non-limiting embodiment, method 500 may include validating the first lab test result as a function of the second lab test result. In another non-limiting embodiment method 500 may include performing each subsequent lab test such as the second lab test and/or third lab test as a function of a time delay. Persons skilled in the art, upon reviewing the entirety of this disclosure, will be aware of the various embodiments of performing multiple tests in the context of improving and enhancing test results.

Still referring to FIG. 5, method 500, at step, 515, may include generating a smart test result as a function of the smart test. The smart test result may include any smart test result as described herein. In a non-limiting embodiment, the smart test result may include an infectivity datum. The infectivity datum may include any infectivity datum as described herein. In some embodiments, generating the smart test result may include generating the smart test result as a function of a smart test machine-learning model. The smart test machine-learning model may include any smart test machine-learning model as described herein. In a non-limiting embodiment, method 500 may include generating the smart test machine-learning model as a function of a plurality of lab test results of the smart test as an input, training the smart test machine-learning model as a function of a smart test training set, wherein the smart test training set includes a disease agent data correlated to an infectivity datum, and outputting the smart test result as a function of the smart test machine-learning model. Persons skilled in the art, upon reviewing the entirety of this disclosure, will be aware of the various embodiments of consolidating and/or combining a plurality of test results in the context of enhance viral testing.

Referring now to FIG. 6, computing device 116 may be configured to retrieve human subject descriptive data. Computing device 116 may be configured to identify human subject descriptive data as a function of unique identifier 428. Computing device 116 may collect information that may include, but is not limited to, personal information about a human subject; medical history; demographic information; information about the human subject's household; or the like. Computing device 116 may be configured to be HIPAA-compliant. For example, computing device 116 may be configured to require two-step authentication. Another non-limiting example, computing device 116 may be configured to require communication. In an embodiment, computing device 116 may be used to create a human subject contact profile. Determining the human subject contact profile may include prompting a human subject for human subject descriptive data. Intake data may have the same form and content as human subject descriptive data. In an embodiment, computing device 116 may be configured to determine the human subject contact profile. The human subject contact profile may be generated by prompting a human subject for human subject intake data and receiving human subject intake data as a function of the prompting. Computing device 116 may by generate a second machine learning process 220 as a function of contact training data. The contact training data correlates intake data elements with a human subject contact profile. The human subject contact profile may be determined as a function of the intake data and the second machine-learning process 220.

Additionally or alternatively, and still referring to FIG. 6. computing device 116 may be configured to collect human subject descriptive data using web portal 600. Computing device 116 may be configured to run in a foreign language. For example, computing device 116 may present instructions and accept responses in Spanish, Chinese-Mandarin, Chinese Cantonese, Japanese, French, Italian, German, and the like. As an example, webportal 600 may ask a human subject a series of questions where the human subject would be the subject of a SARS-CoV-2 test. Human subject descriptive data may be the same as human subject intake data. FIGS. 6A-L shows an exemplary embodiment of the information that may be collected using webportal 600.

Figures 6A, 6B:
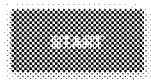
FIG. 6A-6L are representative screenshots depicting various aspects of an exemplary human subject data collected in accordance with this disclosure.

FIG. 6A shows the initial screen that a human subject may see upon entering webportal 600. FIG. 6B shows a screen that may introduce the user to the process of human subject acquisition. Initially, a human subject may provide consent to use the data collected. The human subject may be advised that they will answer questions to establish commonalties and difference among the population of human subjects. The human subject may be reminded that they need to enter unique identifier 428 in webportal 600. The human subject may be reminded that they will receive the results of the testing in a report.

Figure 6C:
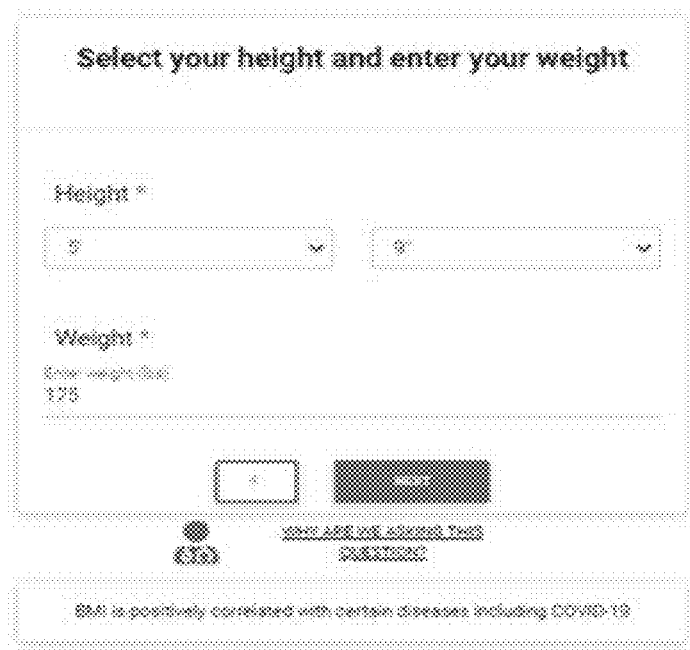

FIG. 6C may prompt the human subject to enter their height and weight. This window may be for the user to enter the data as, for example, a free text. The window may also be configured for the user to move a marker in a graph to the appropriate response.

Figure 6D:
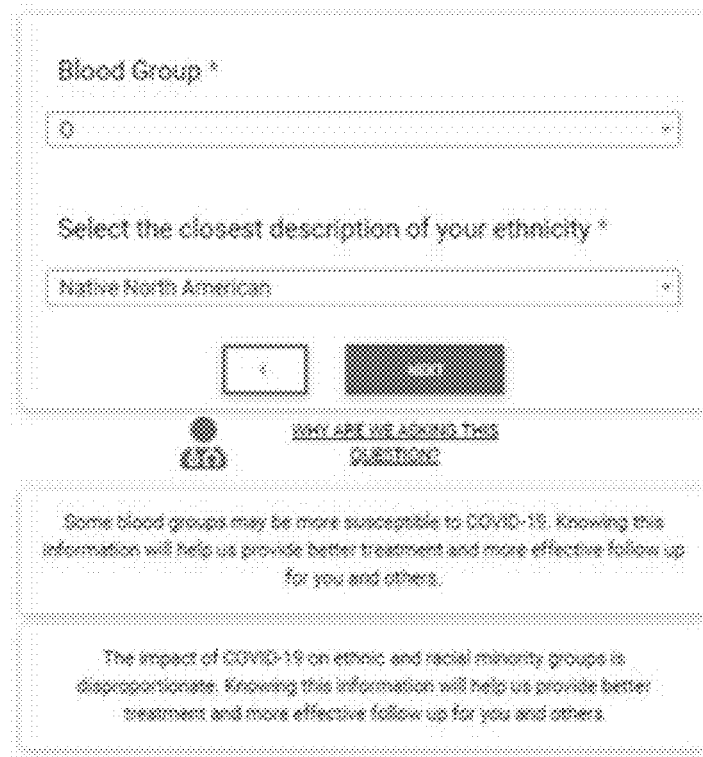

FIG. 6D shows where a human subject webportal 600 may select their blood group. This entry may be made, for example, from a drop-down menu, a free text field for the human subject to enter the appropriate blood group, or the like. The human subject may be prompted to select their ethnicity. This entry may be made, for example, from a drop-down menu, a free text field where the human subject may enter the appropriate ethnicity. For example, a human subject may select or enter "white" as their ethnicity. Other selection that a human subject may select or enter include, but not limited to "Black or African American," "American Indian or Alaska Native," "Asian," "Native Hawaiian and Other Pacific Islander," and the like.

Figure 6E:
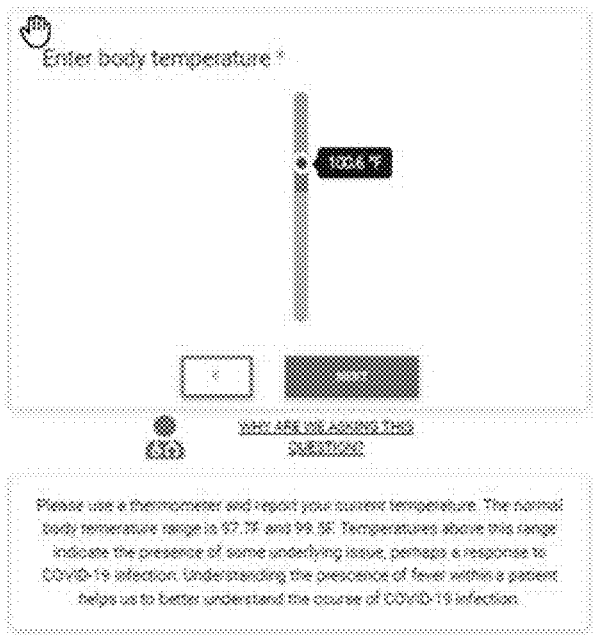

FIG. 6E may ask the human subject to enter their body temperature. The human subject may be presented, for example, with a slider where they can choose their approximate body temperature. Another non-limiting example may present the user with a blank form for the user to enter the value of their body temperature.

Figure 6F:
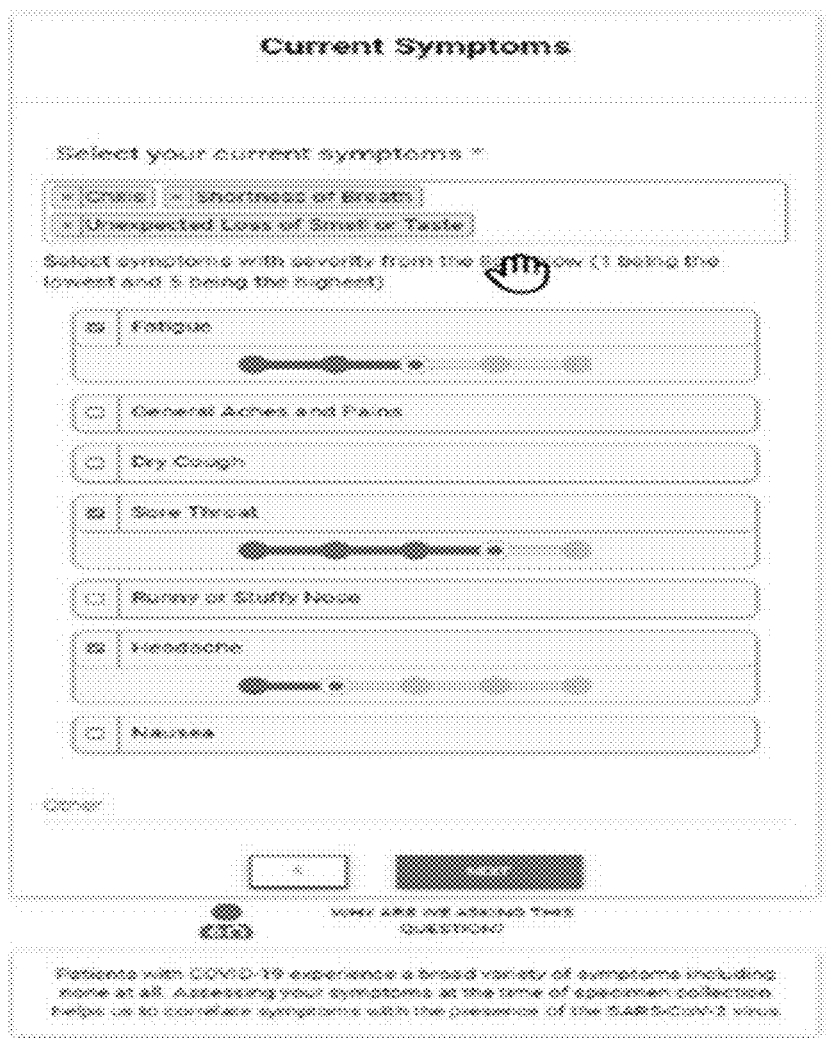

FIG. 6F may allow the human subject to enter their symptoms and the severity of the symptoms. As a non-limiting example, the human subject may select "Nausea" as one of their symptoms. The human subject may select the severity of the symptom, in this case nausea, by selecting from a range between 1 and 4 where 1 is the lowest meaning a mild symptom to a 4 which may indicate that the symptom is severe. The window may be configured for the human subject to click on a symptom. The window may be configured as a free text window where the human subject enters their symptoms as text in the window.

Figures 6G, 6H:

FIG. 6G may allow the user to enter any underlying or pre-existing condition. For example, a human subject may select "Diabetic" and/or "High Blood Pressure." The human subject may, but not limited to, select their pre-existing conditions. The human subject may enter their pre-existing conditions as free text.

Figure 6I:

FIG. 6H may ask the human subject to enter the number of people living in the same household as the human subject. The window may group the number of people living in a household by age range. For example, the window may ask the human subject the number of people with age range 0-19 living in the same household. The human subject may enter the number of people residing in the same household as the human subject of age ranging from 20-39 of age ranging from 40-59 of age 60 or higher, or the like. The window may be configured for the human subject to enter the value for an age range of people residing in a household as free text. The window may also be configured for the human subject to select a value from a drop-down menu, or the like. In FIG. 6H, the human subject may enter the number of pets residing in the same household as the human subject. For example, a human subject may select from a drop-down menu the number of pets in their household. The window may also be configured to accept a numerical value for the number of pets as a free text. FIG. 6I may allow a human subject to enter a value for the number of people the human subject may have talked to that were not wearing a mask. For example, the window may be configured to allow the human subject to enter a numerical value as an answer. The window may be configured to allow, for example, the human subject to select the answer from a drop-down menu. In FIG. 6I, the human subject may be asked to enter their exposure to another person with, for example, SARS-CoV-2. The human subject may select the answer from a drop-down menu containing various numerical values. The window may be configured, for example, to allow the user to enter a numerical value as free text.

In FIG. 6I, the human subject may be asked to describe their work setting. For example, a human subject may respond with an answer that the human subject works in a healthcare environment. The human subject may select an answer from a drop-down menu of choice, enter the answer as free text or the like.

Figure 6J:

In FIG. 6J, the user is prompted to enter the medications or over-the-counter drugs that the human subject is taking. For example, a human subject may start entering a medication, and the window may offer the human subject a choice of medications containing the same root that the user entered where the user then makes a selection. The window may be configured to allow the user to enter the entire name of the medication as free text.

Figures 6K, 6L:
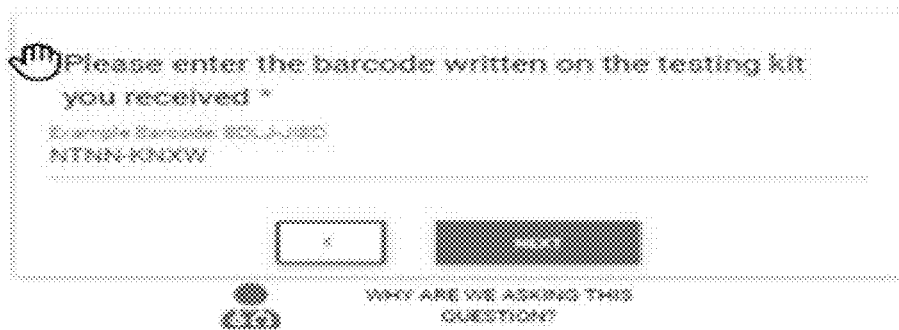

In FIG. 6K, the human subject may enter unique identifier 428 into a window in webportal 600. For example, the human subject may enter a barcode that may be included in collection bag 404. The human subject may enter the value of unique identifier 428 in free-text form. In another non-limiting example, the human subject may begin typing the barcode where the web portal 600 may present the human subject with potential values for the barcode where the human subject can select their barcode. In another non-limiting example, webportal 600 may allow the user to use a mobile device equipped with a scanning device to take an image of the barcode and attach the image to the window. The human subject may be prompted to enter an image file in the window. The image file may be formatted as jpg, png, gif, .pdf, or the like. The window may be configured with a recorder option where the recorder option may allow the human subject to record using their voice the value of the barcode. In FIG. 6L, the human subject may receive an acknowledgement of the submission.

Figure 7:
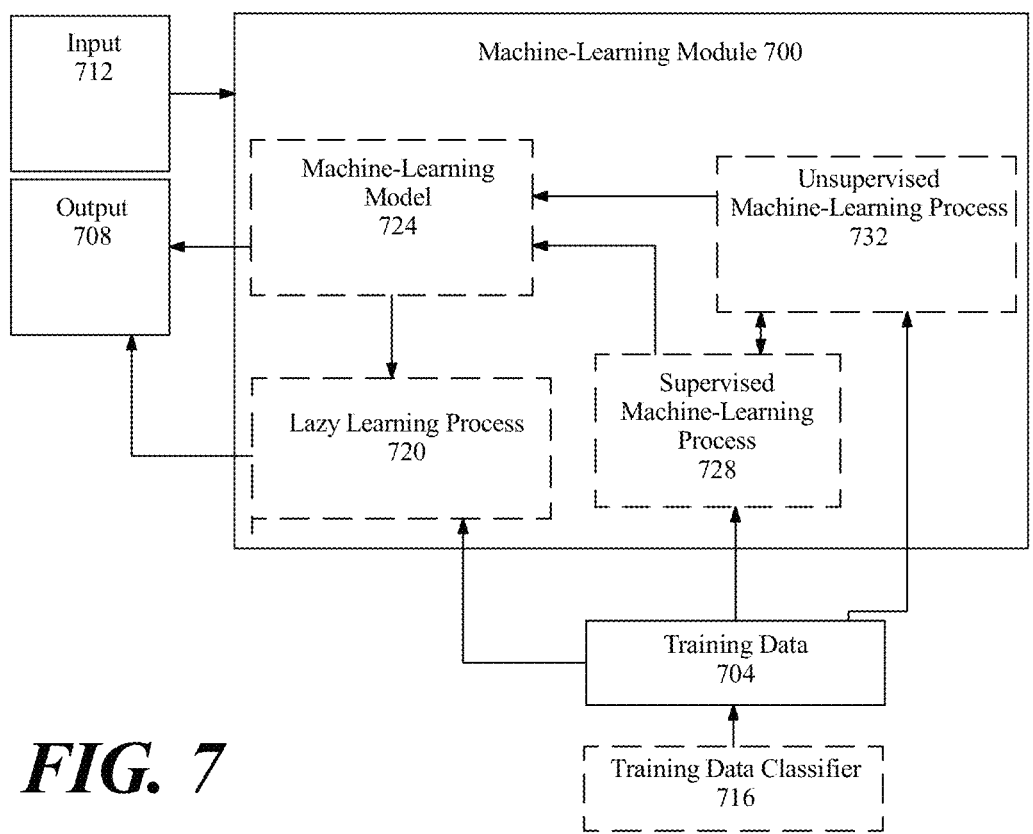
FIG. 7 is a block diagram of an exemplary embodiment of a machine-learning module.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 700 may generate a classifier using a classification algorithm, defined as a processes whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 716 may classify elements of training data to various severity levels of a disease agent and/or phenomena for which a subset of training data may be selected.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as output, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
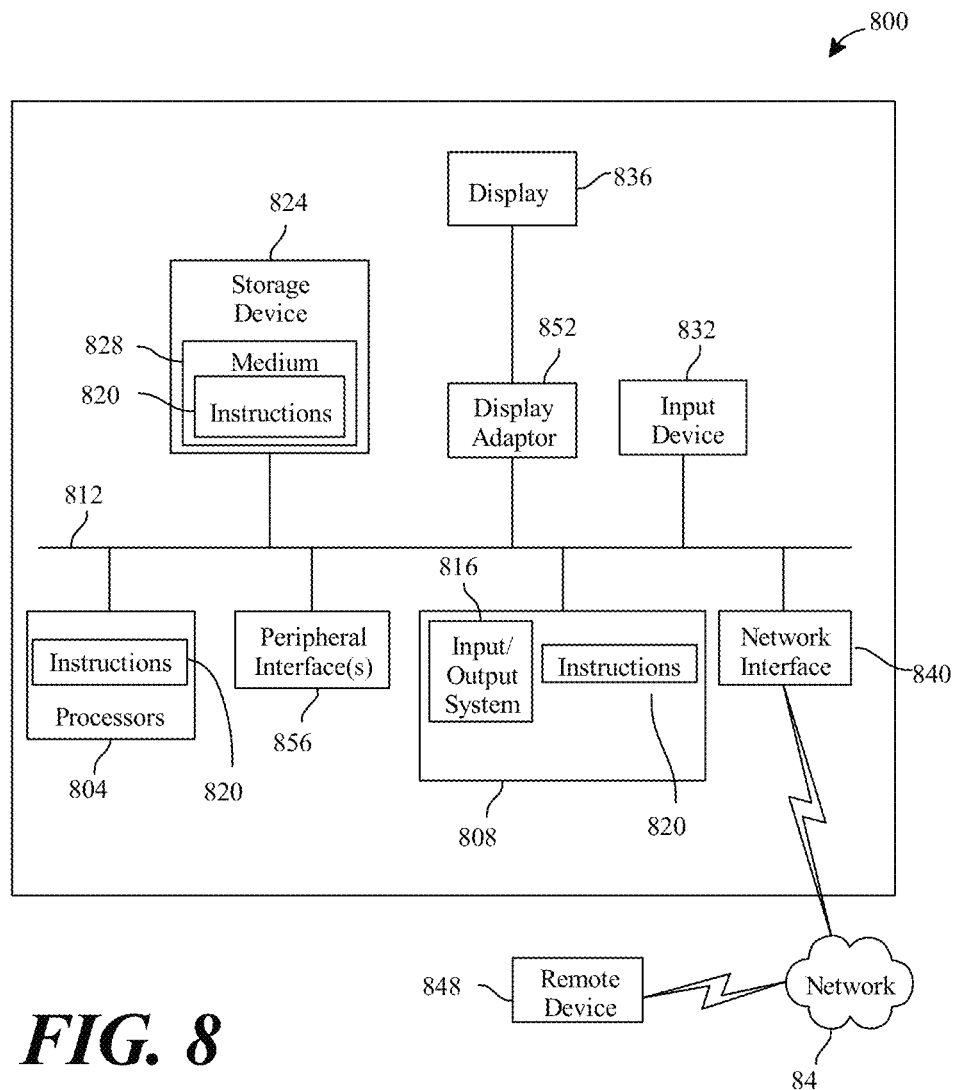
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for second lab testing of genetic materials, the system comprising a computing device configured to:
   receive a specimen from a human subject;
   extract a sequence of genetic material from the specimen as a function of an automatic robot;
   perform a smart test on the sequence of genetic material from the specimen, the smart test comprising:
      a first lab test, wherein the first lab test is configured to generate a first lab test result identifying a first disease agent;
      a second lab test, wherein the second lab test is configured to identify a second disease agent, wherein identifying the second disease agent comprises:
         training a second lab machine-learning model as a function of a second lab test training set, wherein the second lab test training set comprises a human subject descriptive data with a second disease agent; and
         outputting, as a function of the second lab machine-learning model, a second lab test result identifying the second disease agent using specimen data as an input; and
   generate a smart test result as a function of the smart test.

2. The system of claim 1, wherein the specimen comprises:
   genetic material collected from the human subject using a collection device and stored in a collection carrier; and
   a unique identifier on the collection carrier.

3. The system of claim 1, wherein the specimen is configured to be stored in a transfer medium, wherein the transfer medium is configured to preserve the specimen for the plurality of lab tests.

4. The system of claim 1, wherein the second lab test is performed as a function of a time delay.

5. The system of claim 1, wherein the second lab test is performed independently from the first lab test.

6. The system of claim 1, wherein the computing device is further configured to validate the first lab test result as a function of the second lab test result.

7. The system of claim 1, wherein the smart test further comprises a third lab test.

8. The system of claim 1, wherein the smart test result is generated as a function of a smart test machine-learning model, the smart test machine-learning model configured to:
   receive a plurality of lab test results from the smart test as an input;
   train the smart test machine-learning model as a function of a smart test training set, wherein the smart test training set comprises a disease agent data correlated to an infectivity datum; and
   output the smart test result.

9. The system of claim 1, wherein the infectivity datum comprises a measured coronavirus data.

10. A method for second lab testing of extracted samples, the method comprising:
    receiving, by a computing device, a specimen from a human subject;
    extracting a sequence of genetic material from the specimen as a function of an automatic robot;
    performing a smart test on the sequence of genetic material from the specimen, the smart test comprising:
       a first lab test, wherein the first lab test is configured to generate a first lab test identifying a first disease agent;
       a second lab test, wherein the second lab test is configured to generate a second lab test identify a second disease agent, wherein identifying the second disease agent comprises:
          training a second lab machine-learning model as a function of a second lab test training set, wherein the second lab test training set comprises a human subject descriptive data with a second disease agent; and
          outputting, as a function of the second lab machine-learning model, the second lab test result using specimen data as an input; and
    generating a smart test result as a function of the smart test.

11. The method of claim 10, wherein the specimen comprises:
    genetic material collected from the human subject using a collection device and stored in a collection carrier; and
    a unique identifier on the collection carrier.

12. The method of claim 10, wherein the specimen is configured to be stored in a transfer medium, wherein the transfer medium is configured to preserve the specimen for the plurality of lab tests.

13. The method of claim 10, wherein the second lab test is performed as a function of a time delay.

14. The method of claim 10, wherein the second lab test is performed independently from the first lab test.

15. The method of claim 10, wherein the method further comprises validating the first lab test result as a function of the second lab test result.

16. The method of claim 10, wherein performing the smart test further comprises performing a third lab test.

17. The method of claim 10, wherein generating the smart test result comprises:
    generating a smart test machine-learning model as a function of a plurality of lab test results of the smart test as an input;
    training the smart test machine-learning model as a function of a smart test training set, wherein the smart test training set comprises a disease agent data correlated to an infectivity datum; and
    outputting the smart test result as a function of the smart test machine-learning model.

18. The method of claim 10, wherein the infectivity datum comprises a measured coronavirus data.

* * * * *